US00PP15793P3

(12) United States Plant Patent
Grummons et al.

(10) Patent No.: US PP15,793 P3
(45) Date of Patent: Jun. 14, 2005

(54) **PLANT PATENT FOR *DELOSPERMA* PLANT NAMED 'WHITE NUGGET'**

(50) Latin Name: *Delosperma basuticum*
Varietal Denomination: White Nugget

(75) Inventors: Kelly Grummons, Lakewood, CO (US); Cheryl Vestal, Arvada, CO (US)

(73) Assignee: Paulino Gardens, Inc., Denver, CO (US)

( * ) Notice: Subject to any disclaimer, the term of this patent is extended or adjusted under 35 U.S.C. 154(b) by 229 days.

(21) Appl. No.: 10/143,187

(22) Filed: May 9, 2002

(65) Prior Publication Data

US 2003/0213039 P1 Nov. 13, 2003

(51) Int. Cl.[7] ..... A01H 5/00
(52) U.S. Cl. ..... Plt./263

(58) Field of Search ..... Plt./263

(56) References Cited

U.S. PATENT DOCUMENTS

PP13,876 P2 * 6/2003 Kelaidis ..... Plt./263

* cited by examiner

*Primary Examiner*—Bruce R. Campell
*Assistant Examiner*—W C Haas
(74) *Attorney, Agent, or Firm*—The McCallum Law Firm, LLC; Jennifer M. McCallum, Esq.

(57) ABSTRACT

The present invention relates to a new and distinct variety of *Delosperma* named 'White Nugget', the novel characteristics of which reside particularly in its low and compact growing pattern, compact glassy pale foliage, unique white flower, exceptional cold-heartiness, repeated blooming pattern throughout the spring and ability to grow well in a wide-variety of soils and regions.

2 Drawing Sheets

Botanical classification/cultivar designation: *Delosperma basuticum* cultivar White Nugget.

BACKGROUND OF THE INVENTION

The present invention relates to new and distinct cultivar of Ice Plant, botanically known as *Delosperma*, and referred to by the cultivar name 'White Nugget'.

The new cultivar was selected from seedlings which resulted from a cross of *Delosperma* 'Gold Nugget' with an unknown variety of *Delosperma*, and was selected because of its pure white color and exceptional cold-heartiness.

The new cultivar was first discovered by Kelly Grummons in 1996 at Paulino Gardens of Denver, Colo. It was then asexually reproduced in 1997 by Cheryl J. Vestal at Paulino Gardens. Asexual reproduction of the new cultivar by terminal cuttings has shown that the unique features of this new *Delosperma* are stable, and are reproduced true to type in successive propagations.

The unique characteristics of 'White Nugget' have been repeatedly observed and are determined to be basic characteristics of this cultivar, which in combination, distinguish this *Delosperma* from other *Delosperma* species, such as the cultivar *Delosperma* 'Gold Nugget'.

An interesting characteristic of this new variety is its low, compact spreading habit. 'White Nugget' is consistently lower and more dense-growing than the other commonly grown *Delospermas* commercially available and known to the inventor, such as *D. cooperi, D. nubigenum* or *D. foribundum.*

Another interesting characteristic of the new variety is the pale foliage. 'White Nugget' has slightly less pigment in the foliage than other ice plants, like many albino sports.

Another interesting characteristic of the new variety is the pure white flowers. Flowers of 'White Nugget' are pure white and do not contain any other pigment. All other commonly cultivated *Delosperma* are pink or an impure white. In addition, other varieties of *Delosperma* that display white flowers do not display cold-heartiness and are also somewhat shrubby in appearance. These other varieties are easily distinguishable from the new variety described herein.

Another interesting characteristic of the new variety is its exceptional cold-heartiness. 'White Nugget' exhibits unusual cold tolerance when compared to other *Delosperma* species, exhibiting hardiness to at least 20 degrees Fahrenheit below freezing.

Another interesting characteristic of the new variety is its early flowering season. 'White Nugget' produces blooms in early spring and they last until well into the summer. They bloom much earlier and also bloom much longer than any other variety of *Delosperma*, known to the inventor, except for 'Gold Nugget'.

BRIEF SUMMARY OF THE INVENTION

The principle novel characteristic of the new variety of *Delosperma* is its pure white flower. The new variety of *Delosperma* is further characterized by its low, compact spreading habit, pale foliage, exceptional cold-heartiness and early flowering season. All of these characteristics work to provide a variety of *Delosperma* that is visually pleasing with its abundance of white flowers and easy to grow due to its ability to spread easily and withstand cold temperatures.

BRIEF DESCRIPTION OF THE PICTURES

The accompanying photographic drawings show typical flower and leaf characteristics of 'White Nugget', with the colors being as nearly true as possible with illustrations of this type. The distinctive characteristics of the new variety are exemplified in the accompanying illustrations, wherein.

DETAILED BOTANICAL DESCRIPTION

Figure 1:
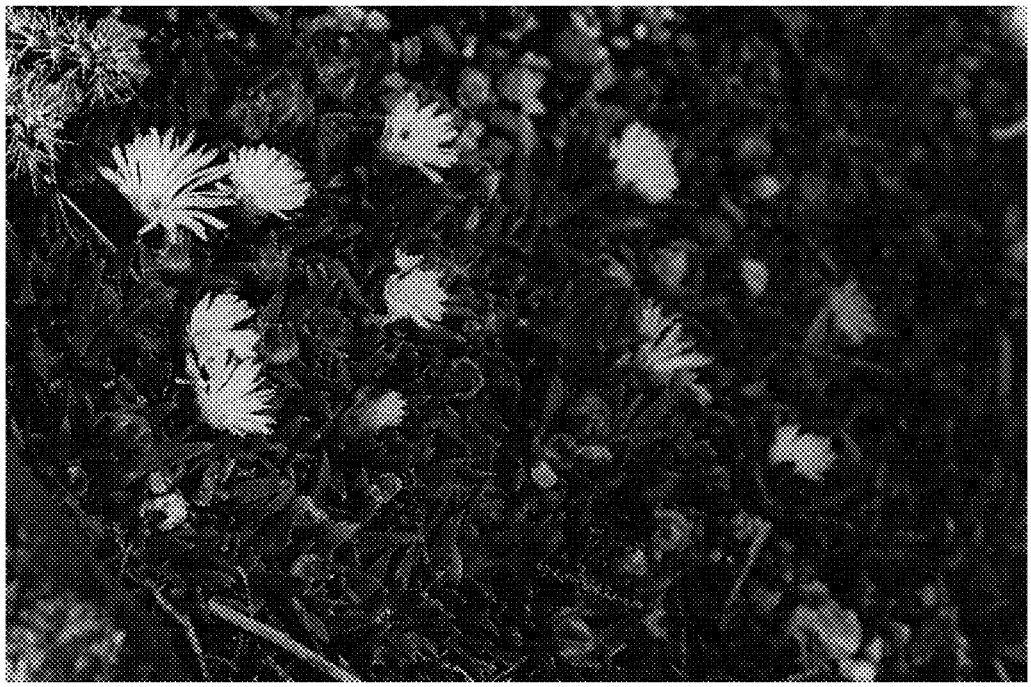
FIG. 1 shows 'White Nugget' in bloom. Some of the blooms are open and some of the blooms are closed or partially closed.
Figure 2:
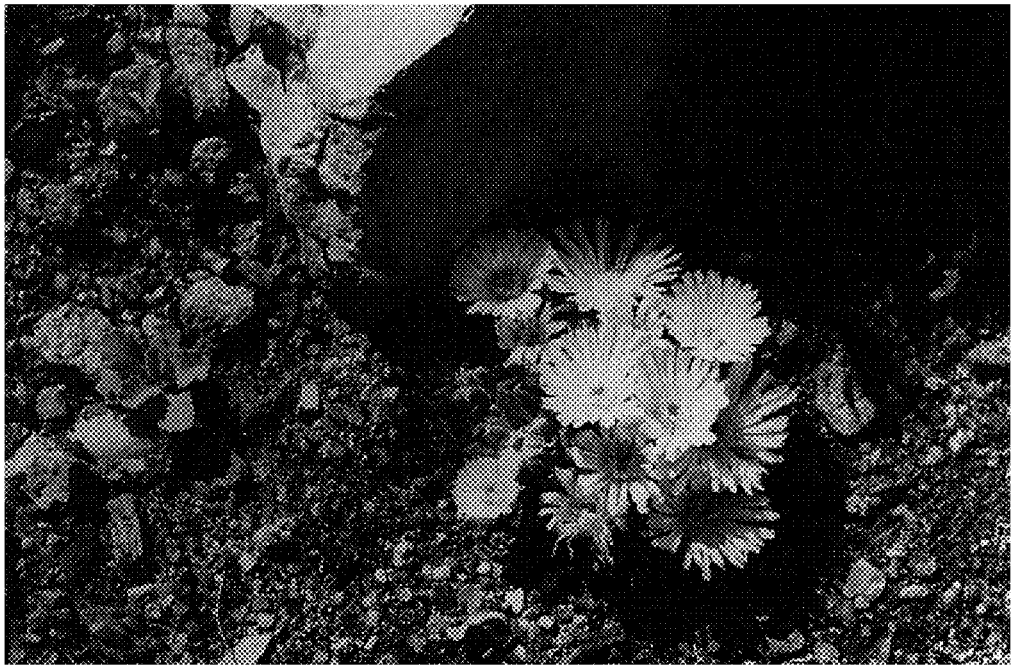
FIG. 2 is a close up of 'White Nugget' in bloom.

The following is a description in some detail of the new variety of *Delosperma*. All color references made in the description refer to The Royal Horticultural Society Colour Chart except where general descriptive terms are used. The color values are determined on two year old plant material grown in Denver, Colo. on Apr. 23, 2002. The plants were grown in a greenhouse during the winter months with average daytime temperatures of about 55° F. and nighttime temperatures of about 40° F. In May, the plants were moved outdoors and grown in average outdoor temperatures for Denver, Colo.

Botanical classification: *Delosperma* cultivar named 'White Nugget'.

Parentage: Clearly *Delosperma* 'Gold Nugget' and possibly another unidentified species of *Delosperma*.

Propagation:

*Type.*—By cuttings.

*Time to initiate roots.*—12 to 16 days. The rate of growth of the roots is approximately 18 cm between May and September.

*Rooting habit.*—Appearance: Fibrous and branching. Form as netting around root ball. Color: white to off-white.

Plant description:

*General appearance.*—Compact spreading mound, (10 to 25 cm spread, 2.5 cm in height) with dense foliage and stemless flower. 'White Nugget' has a basal branching habit and slow to moderate growth rate.

*Foliage description.*—Arrangement: single, alternate, Leaf shape: Oblanceolate, terete, with attenuate leaf base, and rounded or slightly pointed apex. Leaf margin: Smooth. Leaf dimension: Range from 11 to 34 mm in length, and 2.5 to 7 mm wide. Leaf color: Upper surface: Yellow-Green group 147A. Lower surface: Yellow-Green group 147B. Foliage can take on reddish overtones due to anthocyanin during the winter cold months if kept outdoors but stays a strong green if kept under glass.

Flowering description:

*Inflorescence.*—Superficially resembles a daisy with numerous ray-like petals.

*Flowering habit.*—Flowers freely with persistent blooms. A plant of approximately 18 cm exhibits 20–30 flowers at one time.

*Flowering season.*—Blooms heavily from March to May with scattered blooms into the late fall.

*Buds.*—White, RHS 155D pointed, glabrous, 3 to 12 mm in length, 5 mm across.

*Flower color.*—Upper surface opens a uniform white RHS 155D and undersurface is also white RHS 155D. The central flower coloration is white RHS 155D and the flower petals are white RHS 155D.

*Petals.*—Number: 42 to 57. Shape: Lanceolate. Margin: Entire. Tip: Rounded.

*Texture.*—Smooth.

*Appearance.*—Satiny.

*Length.*—7 to 13 mm.

*Width.*—1 to 2 mm.

*Overall flower diameter.*—18 to 28 mm.

*Sepals.*—Length: 7–13 mm. Width: 1–2 mm. Shape: lanceolate with rounded tips. Number: 42–57. Texture: Smooth. Appearance: Satiny.

Reproductive organs: A distinct, five sectioned green ovary that develops into an almost woody, multi-seeded capsule with one style protruding slightly from the corolla. Style branches are white. Filaments are approximately 1.0 cm tall. Anther produce yellow pollen. Neither seed nor fruit production has been observed.

Weather tolerance: High tolerance to rain, wind and temperatures ranging from about −20° F. to 100° F.

We claim:

1. A new and distinctive variety of *Delosperma* plant, substantially as herein shown and described, characterized particularly as to novelty by the unique combination of its ability to exhibit low and compact spreading, exhibit pale foliage, demonstrate compact glossy foliage, exhibit exceptional cold-heartiness, exhibit blooms repeatedly all spring, ability to grow well in a variety of soils, ability to grow well in a variety of regions and its novel white flowers.

* * * * *